United States Patent
Bjurman et al.

(10) Patent No.: US 10,494,594 B2
(45) Date of Patent: Dec. 3, 2019

(54) BIOREACTOR SYSTEM

(71) Applicant: GE Healthcare Bio-Sciences AB, Uppsala (SE)

(72) Inventors: Anders Bjurman, Uppsala (SE); Anders Wilen, Uppsala (SE); Andreas Martin Jorgen Andersson, Uppsala (SE); Fredrik Torgny Nilsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 208 days.

(21) Appl. No.: 15/521,138

(22) PCT Filed: Oct. 22, 2015

(86) PCT No.: PCT/EP2015/074543
§ 371 (c)(1),
(2) Date: Apr. 21, 2017

(87) PCT Pub. No.: WO2016/062833
PCT Pub. Date: Apr. 28, 2016

(65) Prior Publication Data
US 2017/0349870 A1   Dec. 7, 2017

(30) Foreign Application Priority Data
Oct. 23, 2014 (SE) ...................... 1451269

(51) Int. Cl.
*C12M 1/00* (2006.01)
*C12M 3/06* (2006.01)
*C12M 1/34* (2006.01)

(52) U.S. Cl.
CPC ............ *C12M 23/14* (2013.01); *C12M 27/16* (2013.01); *C12M 41/00* (2013.01)

(58) Field of Classification Search
CPC ....... C12M 23/14; C12M 23/26; C12M 27/16
See application file for complete search history.

(56) References Cited

U.S. PATENT DOCUMENTS

2009/0111179 A1   4/2009   Hata et al.
2009/0275114 A1   11/2009  Roll
(Continued)

FOREIGN PATENT DOCUMENTS

CN   102798453 A   11/2012

OTHER PUBLICATIONS

International Search Report and Written Opinion issued in connection with corresponding PCT Application No. PCT/EP2015/074543 dated Jan. 18, 2016.
(Continued)

*Primary Examiner* — Jonathan M Hurst
(74) *Attorney, Agent, or Firm* — Eversheds Sutherland (US) LLP

(57) ABSTRACT

A method for regulating parameters of at least two bioreactor bags individually, which bioreactor bags are provided on one and the same rocking part of a bioreactor system. The method includes the steps of: determining an individual weight of the content in each bioreactor bag at different points in time during processing; regulating one or more parameters in each bioreactor bag in dependence of the individual weights.

4 Claims, 4 Drawing Sheets

(56) References Cited

U.S. PATENT DOCUMENTS

| | | | | |
|---|---|---|---|---|
| 2010/0261226 A1* | 10/2010 | Niazi | .................... | C12M 23/26 |
| | | | | 435/40 |
| 2011/0217690 A1 | 9/2011 | Niazi | | |
| 2012/0258441 A1* | 10/2012 | Gebauer | ............... | C12M 23/14 |
| | | | | 435/3 |
| 2015/0093829 A1* | 4/2015 | Swanda | ................ | C12M 23/22 |
| | | | | 435/420 |
| 2017/0015965 A1* | 1/2017 | Hata | ..................... | C12M 23/14 |

OTHER PUBLICATIONS

International Preliminary Report on Patentability issued in connection with corresponding PCT Application No. PCT/EP2015/074543 dated Apr. 25, 2017.
Chinese Office Action for CN Application No. 201580057543.X dated Apr. 10, 2019 (11 pages with English translation).

* cited by examiner

BIOREACTOR SYSTEM

BACKGROUND

Embodiments of the invention relate to a bioreactor system and to a method for regulating parameters of at least two bioreactor bags provided on one and the same rocking part of the bioreactor system.

A commonly used type of bioreactor for cultivating cells is provided on a rocker unit. Mixing of the culture is accomplished by the wave-induced agitation which is performed by the rocker unit. The conditions in the cell culture can be regulated by different means, for example the temperature can be regulated by providing heat, pH can be regulated by adding acid or base and the amount of liquid/media can be controlled.

Usually one bioreactor bag is provided on the rocker unit and one or more load cells are provided somewhere on the rocker unit in order to measure the weight of the content of the bioreactor bag. The regulation of for example temperature, pH and amount of liquid as described above can then be adapted for different weights. If the weight of the cell culture is changed during the cultivation time (for example by the addition of for example media or acid or base) it is suitable to adapt further regulation/control activities to these new weight conditions. For example more heat is required to increase temperature for a larger volume of cell culture and more base is needed in order to increase pH for a larger volume of cell culture.

A method previously used for being able to individually control two bioreactors provided on the same rocker unit was to assume that the initial weight relationship between the two bags would be maintained throughout the process.

A problem with this previously used method is that if the two bioreactors are controlled individually the content of the two bioreactors will also change individually and the initial weight relationship between the two bags will not be maintained. If a wrong weight is assumed the control method will not be optimal.

SUMMARY

An object of embodiments of the invention is to provide an improved method for individual control of at least two bioreactors provided on one rocking part of a bioreactor system.

A further object of embodiments of the invention is to provide a method and a bioreactor system for individually controlling two bioreactor bags provided on one rocking part where the controlling is individually adapted for each bioreactor bag during run.

This is achieved by a method for regulating parameters of at least two bioreactor bags individually, which bioreactor bags are provided on one and the same rocking part of a bioreactor system, said method comprising the steps of:
  determining an individual weight of the content in each bioreactor bag at different points in time during processing;
  regulating one or more parameters in each bioreactor bag in dependence of the individual weights.

This is also achieved by a bioreactor system comprising a static part, called a rocker base and a rocking part, called a tray, which is rotatably attached to the static part, onto which rocking part at least two bioreactor bags are provided, said system further comprising: determination means for determining an individual weight of the content in each bioreactor bag at different points in time during processing; and regulation means connected to the determination means and being arranged to regulate one or more parameters in each bioreactor bag in dependence of the individual weights.

Hereby the two bags can be controlled individually based on their actual weight at different points in time. This provides improved accuracy and efficiency.

In one embodiment of the invention the step of determining an individual weight of the content in each bioreactor bag comprises: providing a static part of the bioreactor system with load cells measuring the weight of the bioreactor bags, the rocking part and possibly also the static part itself; providing initial weights ($W_{IL}$, $W_{IR}$) of the content of each bioreactor bag to a control unit of the system; storing a value of the weight measured by the load cells with the weights of the content of the bioreactor bags subtracted; utilizing the stored value of the weight measured by the load cells with the weights of the content of the bioreactor bags subtracted and an equation of moment equilibrium and the fact that all forces sums to zero for deriving the individual weights of the content of each bioreactor bag at different points in time.

In one embodiment the storing of a value of the weight measured by the load cells with the weights of the content of the bioreactor bags subtracted is provided by using an initial weight measured by the load cells while the content of the bioreactor bags still is equal to the provided initial weights (WIL, WIR) of the content of each bioreactor bag and subtracting the provided initial weights (WIL, WIR) of the content of each bioreactor bag.

In one embodiment of the invention the method further comprises the step of determining a position of the mass center of the static part and the rocking part together with the bioreactor bags by utilizing an equation for moment equilibrium and the fact that all forces sums to zero and the initial weights of the content of each bioreactor bag, said position of the mass center is used in the determining of an individual weight of the content on each bioreactor bag at different times.

Further embodiments are described in the dependent claims.

DETAILED DESCRIPTION

Figure 1:
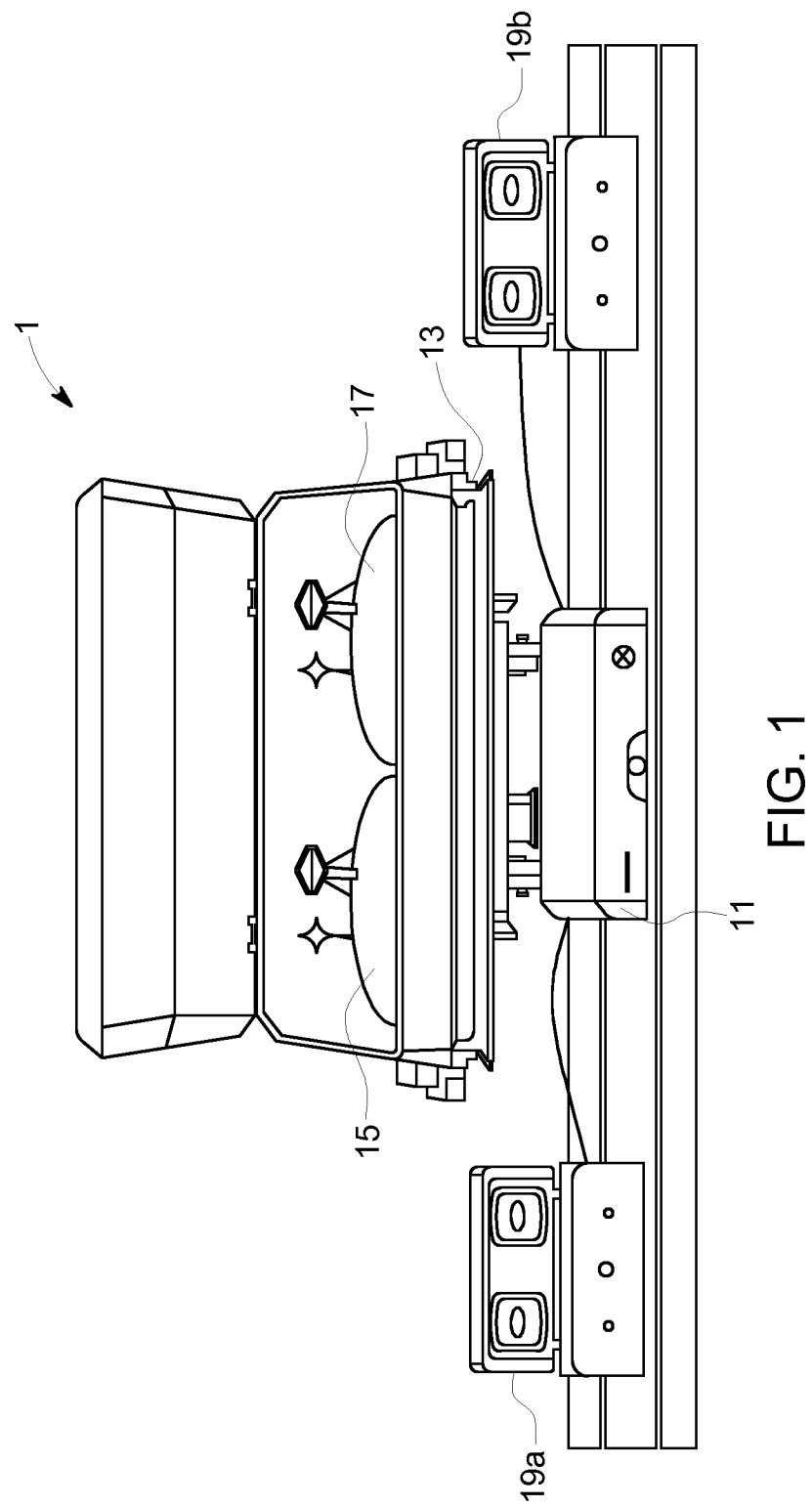
FIG. 1 shows a rocking bioreactor system according to one embodiment of the invention.

FIG. 1 shows a rocking bioreactor system 1 according to one embodiment of the invention. The bioreactor system comprises a static part, also called a rocker base 11, and a rocking part, also called a tray 13, which rocking part is rotatably and possibly also detachably attached to the static part for reciprocal movement around an axis. The bioreactor system comprises also a first and a second bioreactor bag 15, 17 provided on the tray 13. The rocker base 11 is arranged to provide a rocking motion to the tray 13. The bioreactor system comprises further one or more control units 19a, 19b connected to the rocker base 11 and the first and second bioreactor bags 15, 17. The control units are used to control various parameters of the culture such as pH, DO, culture media volume etc. The rocker unit comprises load cells (not visible in the drawings). In one embodiment the rocker unit is standing on the load cells whereby the load cells register the weight of all of the rocker base 11, the tray 13, the first and second bioreactor bags 15, 17 and the contents of the bioreactor bags. In one embodiment of the invention four load cells are provided, one in (or close to) each corner of the rocker unit. However, also three load cells would be possible or more than four. Furthermore the rocker base need not be square or rectangular but could as well be circular or oval or have any other suitable form. In any case the load cells should be distributed under the rocker unit such that the rocker unit rests stably and in order to register the weight.

In another embodiment load cells are instead provided in hinges between the rocker base and the tray. This is described in more detail below in relation to FIG. 3. In that embodiment only two load cells are needed. The weight registered by the two load cells in this embodiment does thus obviously not comprise the weight of the rocker base but only the weight of the tray and the bioreactor bags with content.

According to embodiments of the invention the weight measurements from these load cells together with a number of internal distances in the bioreactor system and also together with an initial weight measurement of the complete system with the weight of the initially provided cell culture (content in the bioreactor bags) subtracted are used for determining the individual weights of the content of the two bioreactor bags at different points in time. As will be discussed in detail below in relation to FIG. 2 equations for moment equilibrium are used for these calculations.

The individual weights of the contents of the first and second bioreactor bags 15, 17 will, according to embodiments of the invention, be used for the controlling/regulation of parameters of the cell culture. For example the temperature can be measured by a temperature sensor and regulated by a heater. In one embodiment the control units 19a, 19b are therefore connected to such temperature sensors provided in connection to the bioreactor bags and to heaters also provided in connection to the bioreactor bags. In another embodiment the temperature regulation is integrated into the rocker unit. All regulation mechanisms could be provided in one or more separately provided control units or some or all of the functions could instead be provided in the rocker base itself. In fact the choice of where to provide control functions is optional and not important. The amount of heat needed for adjusting the temperature is dependent on the amount/weight of cell culture and therefore the temperature control will be more efficient and exact when an accurate weight measurement for each bioreactor bag is used for different points in time. There is no need to have approximately the same volume of culture in the two bags. Furthermore pH can be regulated in the bioreactor bags by adding acid or base. For that purpose the control units 19a, 19b are connected to a pH sensor in each bioreactor bag. Furthermore the control units 19a, 19b are connected to pumps which in turn are connected by tubes to acid/base containers and to the bioreactor bags for delivering of acid and base for regulating the pH in the cell cultures. According to embodiments of the invention also this regulation of pH utilizes the individual weight measurements of the two bioreactor bags at different points in time in order to improve effectiveness and exactness. Another type of control where the individual weight measurements suitably are used is the control of amount of media in the bioreactor bags. Controlling the amount of media in each bag individually is especially important in a fed batch culture and also here the effectiveness and exactness of the control will be improved with the method according to embodiments of the invention. Control of other parameters of the cellbag culture may also be individually done based on the individual weights.

Figure 2:
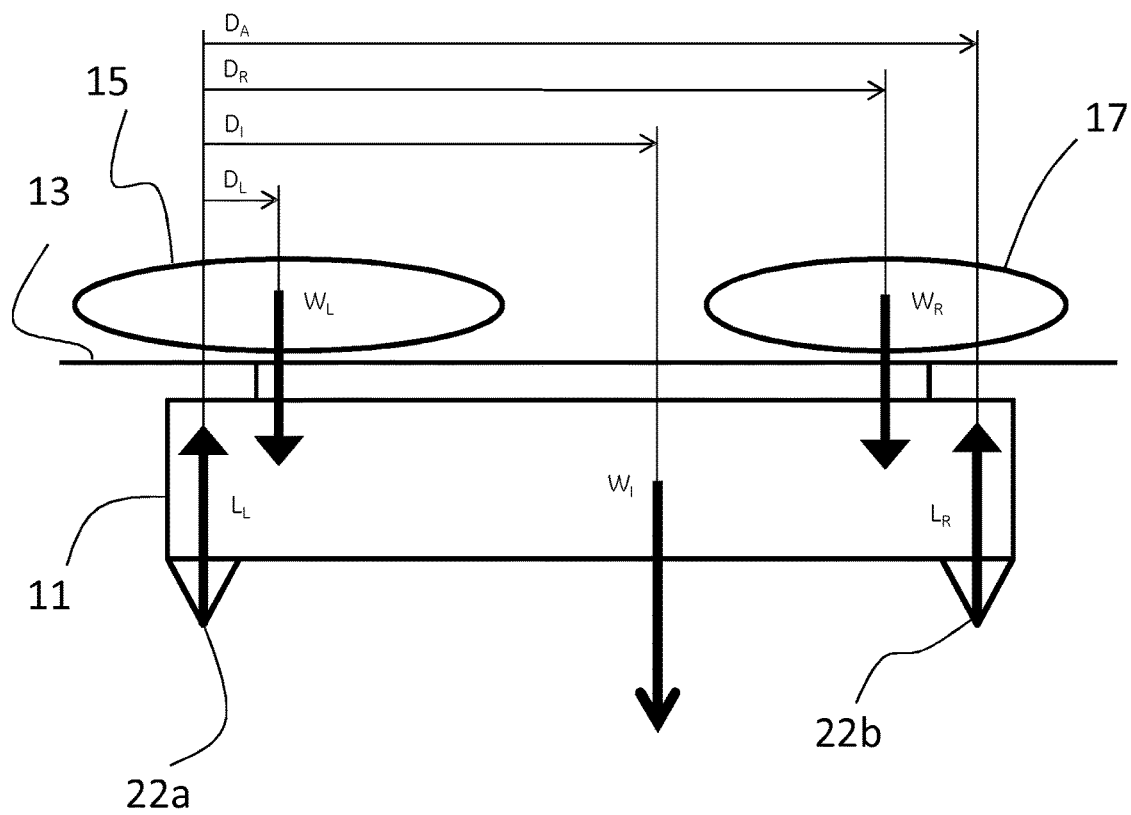
FIG. 2 shows schematically a rocking bioreactor system according to one embodiment of the invention.

FIG. 2 shows schematically a rocking bioreactor system according to one embodiment of the invention. In this embodiment the rocker base 11, which is the static part of the system is standing on four load cells one in each corner (or close to the corners), arranged to measure the weight of the whole system. However, for the purpose of using an equation for moment equilibrium for computing the individual weights of the bioreactor bags content we assume that the two left (referring to the directions in the drawings) load cells are represented by one imaginary left load cell 22a positioned in the middle between the two left corners of the rocker base and showing the sum of the measured values of the two left load cells. In the same way we assume that the two right load cells are represented by one imaginary right load cell 22b positioned in the middle between the two right corners of the rocker base and showing the sum of the measured values of the two right load cells. A tray 13 (rocking part of the system) is seen provided on top of the rocker base 11. This tray 13 is adapted for holding two bioreactor bags, a first bioreactor bag 15 (to the left in the figure) and a second bioreactor bag 17 (to the right in the figure). Furthermore in this view forces acting on the device are illustrated by arrows in the vertical direction and distances used for calculations are illustrated by horizontal arrows as defined below:

$W_L$: Weight of the left bag (first bioreactor) content. May change over time.

$W_R$: Weight of the right bag (second bioreactor) content. May change over time.

$W_I$: Weight of the instrument including tray, empty bags, rocker bas and any lid if used. I.e. everything affecting the load cells except the content of the bags.

$L_L$: Total weight measured by the two left load cells.

$L_R$: Total weight measured by the two right load cells.

$D_A$: Distance between the imaginary left load cell 22a and the imaginary right load cell 22b. This value is constant and defined in the system.

$D_L$: Distance from the imaginary left load cell 22a to a mass center of the first bioreactor bag 15. This value is assumed to be constant but may differ if the bag is not positioned correctly.

$D_R$: Distance from the imaginary left load cell 22a to a mass center of the second bioreactor bag 17. This value is assumed to be constant but may differ if the bag is not positioned correctly.

$D_I$: Distance from the imaginary left load cell 22a to a mass center of the instrument. This value depends slightly on what type of bags that are selected and may possibly be different for different instruments.

According to embodiments of the invention the values of $W_L$ and $W_R$ should be determined dynamically. In order to calculate this we need to use both the fact that the sum of all forces should be zero (equation 1) and an equation for moment equilibrium around the imaginary left load cell 22a (equation 3). Of course the equation for moment equilibrium could be set up around another point.

$$L_L + L_R - W_L - W_R - W_I = 0 \quad \text{(equation 1)}$$

Equation 1 can be written:

$$W_R = L_L + L_R - W_L - W_I \quad \text{(equation 2)}$$

The Torque Equation:

$$-D_A * L_R + D_R * W_R + D_I * W_I + D_L * W_L = 0 \quad \text{(equation 3)}$$

This can be written as:

$$W_L = \frac{D_A * L_R - D_R * W_R - D_I * W_I}{D_L} \quad \text{(equation 4)}$$

Combining equations 2 and 4 gives:

$$W_L = \frac{D_A * L_R - D_R * (L_L + L_R - W_L - W_I) - D_I * W_I}{D_L}$$

$$W_L = \frac{D_A * L_R}{D_L} - \frac{D_R * L_L}{D_L} - \frac{D_R * L_R}{D_L} + \frac{D_R * W_L}{D_L} + \frac{D_R * W_I}{D_L} - \frac{D_I * W_I}{D_L}$$

$$W_L - \frac{D_R}{D_L} * W_L = \frac{D_A * L_R - D_R * L_L - D_R * L_R + D_R * W_I - D_I * W_I}{D_L}$$

Finally this gives $$W_L = \frac{D_A * L_R - D_R * L_L - D_R * L_R + D_R * W_I - D_I * W_I}{D_L - D_R} \quad \text{(equation 5)}$$

The values for $D_I$ and $W_I$ need to be determined. In order to do that the user needs to enter start values for $W_L$ and $W_R$. If the bioreactor bags are empty from the beginning these values should be set to zero.

The value of $W_I$ is calculated using the formula:

$$W_I = L_L + L_R - W_{IL} - W_{IR} \quad \text{(equation 6)}$$

where $W_{IL}$ and $W_{IR}$ are the start values for $W_L$ and $W_R$ as entered by the user. This formula is derived from Equation 1. When calculating $W_I$ values of $L_L$ and $L_R$ needs to be taken at a point in time when $W_L$ and $W_R$ are known, in this case we use $W_{IL}$ and $W_{IR}$ as known in the beginning of the process, i.e. before any controlling is performed to the bioreactor bags. In equation 6 we use the initial values for $L_L$ and $L_R$ when the bioreactor bag contents still is as entered by the user as $W_{IL}$ and $W_{IR}$. This will hereafter be called the initial weight measured by the load cells.

In addition, the equation for moment equilibrium derived from Equation 3 around the imaginary left load cell 22a gives that $$-D_A * L_R + D_R * W_{IR} + D_I * W_I + D_L * W_{IL} = 0 \quad \text{(equation 7)}$$

$$D_I = \frac{-D_L * W_{IL} - D_R * W_{IR} + D_A * L_R}{W_I}$$

Hereby $W_R$ and $W_L$ can be calculated at different points in time using equations 5 and 2 given above. $D_I$ and $W_I$ will be given by the equations 6 and 7.

Figure 3:
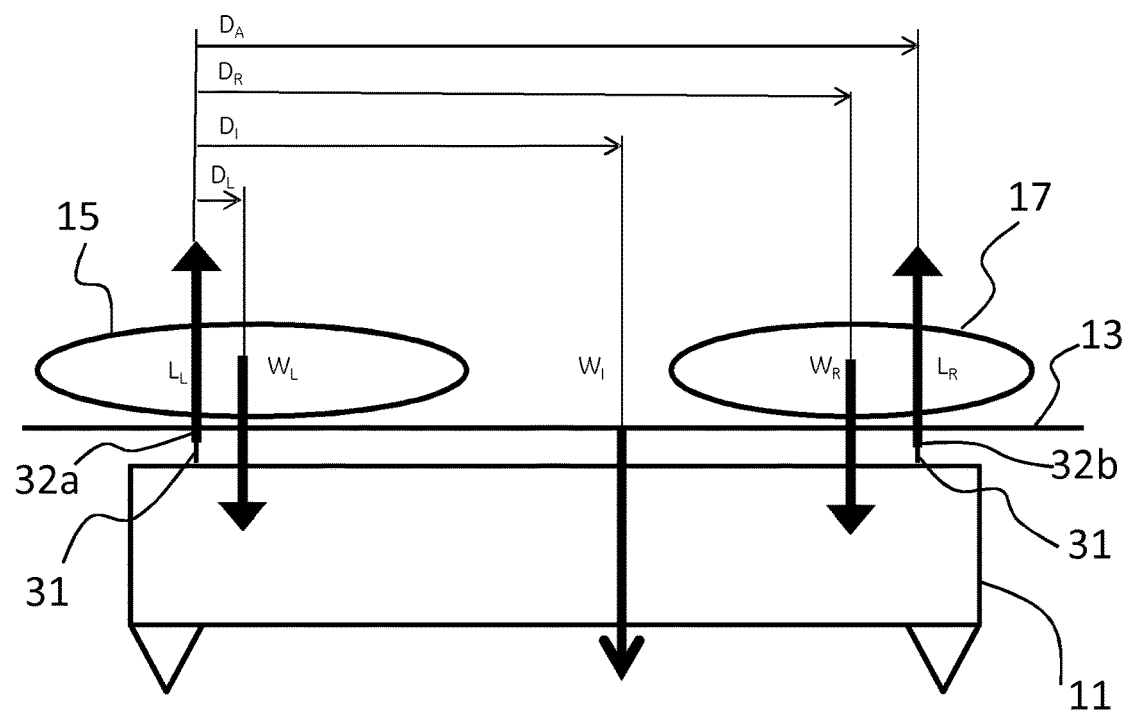
FIG. 3 shows schematically a rocking bioreactor system according to another embodiment of the invention.

FIG. 3 shows schematically a rocking bioreactor system according to another embodiment of the invention. In this embodiment the load cells 32a,b are provided on hinges 31 which are provided between the rocker base 11 and the tray 13. Hereby only two load cells are needed even if more load cells also could be provided if wanted. One load cell is suitably provided in the middle of each hinge and these load cells are thus measuring the weight of the tray 13 and the bioreactor bags 15, 17 (and possibly a lid of used). In the same way as described in relation to the embodiment shown in FIG. 2 forces acting on the device are illustrated by arrows in the vertical direction and distances used for calculations are illustrated by horizontal arrows as defined below:

$W_L$: Weight of the left bag (first bioreactor) content. May change over time.

$W_R$: Weight of the right bag (second bioreactor) content. May change over time.

$W_I$: Weight of the tray, empty bags and any lid if used. I.e. everything affecting the load cells except the content of the bags.

$L_L$: Total weight measured by the left load cell(s).

$L_R$: Total weight measured by the right load cell(s).

$D_A$: Distance between the left load cell 32a and the right load cell 32b. This value is constant and defined in the system.

$D_L$: Distance from the left load cell 32a to a mass center of the first bioreactor bag 15. This value is assumed to be constant but may differ if the bag is not positioned correctly.

$D_R$: Distance from the left load cell 32a to a mass center of the second bioreactor bag 17. This value is assumed to be constant but may differ if the bag is not positioned correctly.

$D_I$: Distance from the left load cell 32a to a mass center of the instrument. This value depends slightly on what type of bags that are selected and may possibly be different for different instruments.

If only two load cells are used the imaginary load cells used for the calculations in relation to the embodiment described in FIG. 2 are not needed. Furthermore $W_I$ does not include the weight of the rocker base. Otherwise all details and calculations are identical and not further described here.

Figure 4:
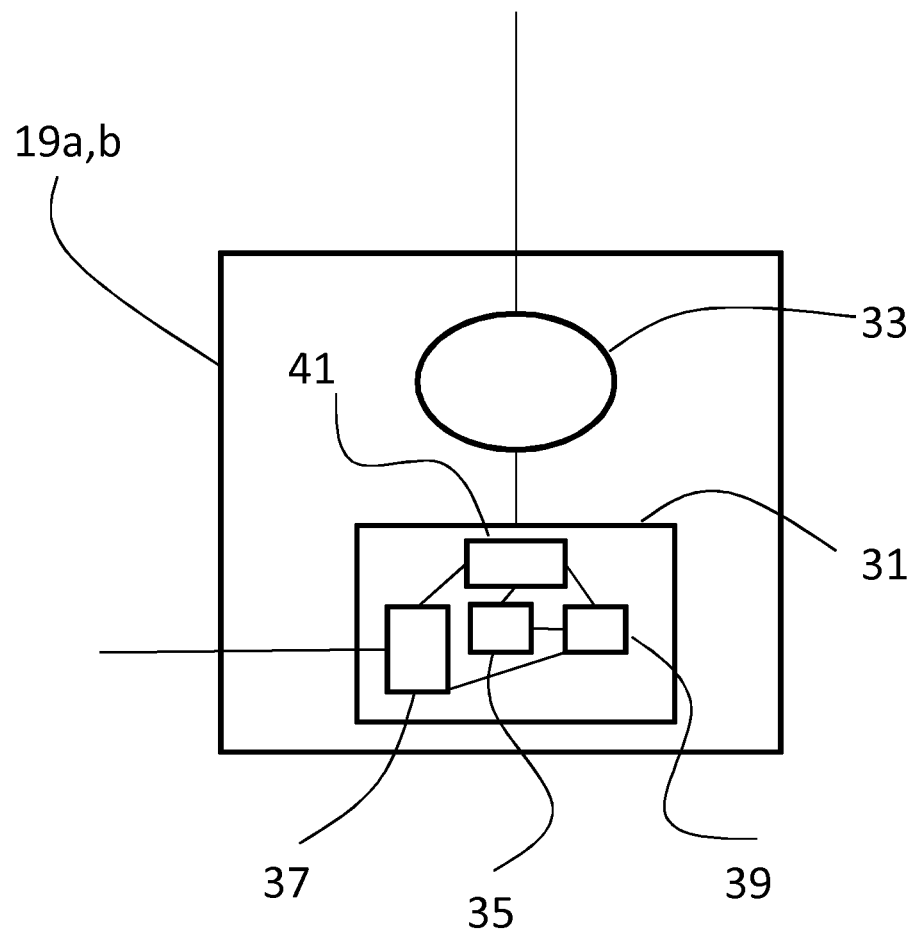
FIG. 4 shows schematically a control unit according to one embodiment of the invention.

A control unit 19a, 19b according to one embodiment of the invention is shown in more detail in FIG. 4. As described above the control/regulation functions could be provided in one or more control units or in the rocker base itself or in both. The control unit 19a, 19b comprises: determination means 31 for determining an individual weight of the content in each bioreactor bag at different points in time during processing; and regulation means 33 connected to the determination means and being arranged to regulate one or more parameters in each bioreactor bag in dependence of the individual weights.

This regulation means could be connected to heaters for regulation of temperature and to acid and base delivery systems for regulation of pH for example.

The determination means further comprises: receiving means 35 for receiving entered values of initial weights of the content of each bioreactor bag; weight receiving means 37 for receiving weight measurements from the load cells; storing means 39 for storing a value of a weight measured by the load cells with the weights of the content of each bioreactor bag subtracted; deriving means 41 for utilizing an equation of moment equilibrium and the fact that all forces sums to zero and the stored value of the weight measured by the load cells with the content of bioreactor bags subtracted for deriving the individual weights of the content of each bioreactor bag at different points in time.

In one embodiment the storing means 39 is arranged to use an initial weight measured by the load cells while the content of the bioreactor bags still is equal to the provided initial weights $W_{IL}$, $W_{IR}$ of the content of each bioreactor bag and subtracting the provided initial weights $W_{IL}$, $W_{IR}$ of the content of each bioreactor bag for storing a value of the weight measured by the load cells with the weights of the content of the bioreactor bags subtracted.

The deriving means is in one embodiment arranged to set up the equation of moment equilibrium around an imaginary load cell 22a provided on the support in between two of the real load cells.

This method of measuring the individual weights of two bioreactor bags in a rocking bioreactor system can also be used for keeping track of the individual weights during filling or emptying of the bioreactor bags. For example in perfusion a specific weight needs to be kept in each of the bioreactor bags while media is added and pumped out during the process. The individual measuring of the weights of the content of the two bioreactor bags can also be used for individual calibration of two pumps.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for regulating parameters of at least two bioreactor bags individually, which bioreactor bags are provided on one and the same rocking part of a bioreactor system, said method comprising the steps of:
    determining an individual weight of the content in each bioreactor bag at different points in time during processing;
    regulating one or more parameters in each bioreactor bag in dependence of the individual weights;
    wherein the step of determining an individual weight of the content in each bioreactor bag comprises:
    providing a static part of the bioreactor system with load cells measuring the weight of the bioreactor bags, the rocking part and possibly also the static part itself;
    providing initial weights (WIL, WIR) of the content of each bioreactor bag to a control unit of the system;
    storing a value of the weight measured by the load cells with the weights of the content of the bioreactor bags subtracted;
    utilizing the stored value of the weight measured by the load cells with the weights of the content of the bioreactor bags subtracted and an equation of moment equilibrium and the fact that all forces sums to zero for deriving the individual weights of the content of each bioreactor bag at different points in time.

2. A method according to claim 1, wherein the storing of a value of the weight measured by the load cells with the weights of the content of the bioreactor bags subtracted is provided by using an initial weight measured by the load cells while the content of the bioreactor bags still is equal to the provided initial weights (WIL, WIR) of the content of each bioreactor bag and subtracting the provided initial weights (WIL, WIR) of the content of each bioreactor bag.

3. A method according to claim 1, further comprising the step of determining a position of the mass center of the static part and the rocking part together with the bioreactor bags by utilizing an equation for moment equilibrium and the fact that all forces sums to zero and the initial weights of the content of each bioreactor bag, said position of the mass center is used in the determining of an individual weight of the content on each bioreactor bag at different times.

4. A method according to claim 1, further comprising:
    providing load cells under the static part of the bioreactor system distributed such that the static part rests steadily on the load cells.

* * * * *